United States Patent
Baleine (10) Patent No.: US 8,174,699 B2
(45) Date of Patent: May 8, 2012

(54) FLUID DETECTION IN TURBINE ENGINE COMPONENTS

(75) Inventor: Erwan Baleine, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 105 days.

(21) Appl. No.: 12/841,305

(22) Filed: Jul. 22, 2010

(65) Prior Publication Data

US 2012/0020769 A1 Jan. 26, 2012

(51) Int. Cl.
*G01N 21/00* (2006.01)

(52) U.S. Cl. .................. 356/432; 356/135; 356/436

(58) Field of Classification Search .......... 356/432–440, 356/128–137; 73/116, 152.11
See application file for complete search history.

(56) References Cited

U.S. PATENT DOCUMENTS

| | | |
|---|---|---|
| 3,323,410 A | 6/1967 | Waters |
| 5,172,186 A | 12/1992 | Hosoe |
| 5,305,089 A | 4/1994 | Hosoe |
| 6,923,048 B2 * | 8/2005 | Willsch et al. ............. 73/112.01 |
| 7,733,490 B2 * | 6/2010 | Goodwin et al. ............. 356/436 |
| 7,924,424 B2 * | 4/2011 | Erickson et al. ............. 356/432 |
| 2008/0101683 A1 | 5/2008 | Zombo et al. |
| 2010/0149523 A1 * | 6/2010 | Heideman et al. ........... 356/128 |
| 2011/0081562 A1 * | 4/2011 | Parakulam et al. ............ 429/50 |

FOREIGN PATENT DOCUMENTS

EP 0809098 A1 11/1997

* cited by examiner

*Primary Examiner* — Hoa Pham (57) ABSTRACT

A system for detecting the presence of one or more fluids in a rotating component of a gas turbine engine. A first reflector structure includes a first face that receives light from the light source. The first reflector structure reflects at least a substantial portion of the received light from the light source if a second face thereof is in the presence of a first fluid and does not reflect a substantial portion of the received light from the light source if the second face is in the presence of a second fluid. A reflection receiver structure receives light reflected by the first reflector structure. If the reflection receiver structure receives a first predetermined amount of light reflected by the first reflector structure it can be determined that the second face of the first reflector structure is not in the presence of the second fluid.

20 Claims, 5 Drawing Sheets

FLUID DETECTION IN TURBINE ENGINE COMPONENTS

FIELD OF THE INVENTION

The present invention relates to detecting one or more fluids in rotating components in turbine engines.

BACKGROUND OF THE INVENTION

Turbomachines, such as gas turbine engines, generally include a compressor section, a combustor section and a turbine section. A rotor is typically provided extending axially through the sections of the gas turbine engine and includes structure supporting rotating blades in the compressor and turbine sections. In particular, a portion of the rotor extending through the turbine section comprises a plurality of turbine disks joined together wherein each turbine disk is adapted to support a plurality of turbine blades. Similarly, a portion of the rotor extending through the compressor section comprises a plurality of compressor disks joined together wherein each compressor disk is adapted to support a plurality of compressor blades. The portions of the rotor in the turbine and compressor sections are connected by a torque tube.

In a known construction of a gas turbine engine, fluids, such as water or oil, may undesirably leak into rotating components of the engine, such as the torque tube. As fluids may cause damage to such rotating components, it is desirable to detect when fluids are present therein.

SUMMARY OF THE INVENTION

In accordance with an aspect of the invention, a system is provided for detecting the presence of one or more fluids in a rotating component of a gas turbine engine. The system comprises a light source that emits light, a first reflector structure, and a reflection receiver structure. The first reflector structure is coupled to the rotating component and has a first face and a second face. The first face receives light from the light source. The first reflector structure reflects at least a substantial portion of the received light from the light source if the second face is in the presence of a first fluid and does not reflect a substantial portion of the received light from the light source if the second face is in the presence of a second fluid, the second fluid having an index of refraction that is greater than an index of refraction of the first fluid. The reflection receiver structure receives light reflected by the first reflector structure. If the reflection receiver structure receives a first predetermined amount of light reflected by the first reflector structure it can be determined that the second face of the first reflector structure is not in the presence of the second fluid.

The reflection receiver structure may comprise a lens, which lens may collimate the light from the light source and direct the collimated light toward the first reflector structure.

The light source may comprise a laser source that emits a laser beam.

The first reflector structure may function as a retroreflector when the first reflector structure second face is in the presence of the first fluid.

The reflector structure may comprise a corner cube prism.

The light source may not rotate with the rotating component and the first reflector structure.

The first fluid may be air and the second fluid may be water or oil.

The system may further comprise a second reflector structure coupled to the rotating component and spaced circumferentially from the first reflector structure. The second reflector structure includes a first face and a second face, the first face receiving light from the light source. The second reflector structure reflects at least a substantial portion of the received light from the light source if the second face is in the presence of the first fluid, reflects at least a substantial portion of the received light from the light source if the second face is in the presence of the second fluid, and does not reflect a substantial portion of the received light from the light source if the second face is in the presence of a third fluid, the third fluid having an index of refraction that is greater than the index of refraction of the second fluid. The reflection receiver structure receives light reflected by the second reflector structure. If the reflection receiver structure receives a second predetermined amount of light reflected by the second reflector structure it can be determined that the second face of the second reflector structure is not in the presence of the third fluid.

The first fluid may be air, the second fluid may be water, and the third fluid may be a type of oil.

The system may further comprise a third reflector structure coupled to the rotating component and spaced circumferentially from the first and second reflector structures. The third reflector structure includes a first face and a second face, the first face receiving light from the light source. The third reflector structure reflects at least a substantial portion of the received light from the light source if the second face is in the presence of the first fluid, reflects at least a substantial portion of the received light from the light source if the second face is in the presence of the second fluid, and reflects at least a substantial portion of the received light from the light source if the second face is in the presence of the third fluid. The reflection receiver structure receives light reflected by the third reflector structure. If the reflection receiver structure receives a third predetermined amount of light reflected by the third reflector structure it can be determined that the system is functioning properly.

The first reflector structure may comprise a corner cube prism formed from a first material having a first index of refraction. The second reflector structure may comprise a corner cube prism formed from a second material having a second index of refraction greater than the first index of refraction. The third reflector structure may comprise a corner cube prism formed from a third material having a third index of refraction greater than the second index of refraction.

In accordance with another aspect of the invention, a system is provided for detecting the presence of one or more fluids in a rotating component of a gas turbine engine. The system comprises a light source that emits light, at least one first reflector structure, at least one second reflector structure, and a reflection receiver structure. The at least one first reflector structure is coupled to the rotating component. Each first reflector structure has a first face and a second face, the first face receiving light from the light source. Each first reflector structure reflects at least a substantial portion of the received light from the light source if the second face is in the presence of a first fluid and does not reflect a substantial portion of the received light from the light source if the second face is in the presence of a second fluid. The at least one second reflector structure is coupled to the rotating component and spaced circumferentially from each first reflector structure. Each second reflector structure has a first face and a second face, the first face receiving light from the light source. Each second reflector structure reflects at least a substantial portion of the received light from the light source if the second face is in the presence of the first fluid, reflects at least a substantial portion of the received light from the light source if the second face is in the presence of the second fluid, the second fluid having an index of refraction that is greater than an index of refraction of the first fluid, and does not reflect a substantial portion of the received light from the light source if the second face is in the presence of a third fluid, the third fluid having an index of refraction that is greater than the index of refraction of the second fluid. The reflection receiver structure receives light reflected by each of the first and second reflector structures. If the reflection receiver structure receives a first predetermined amount of light reflected by at least one of the first reflector structures it can be determined that the second face of the at least one of the first reflector structures is not in the presence of the second fluid. If the reflection receiver structure receives a second predetermined amount of light reflected by at least one of the second reflector structures it can be determined that the second face of the at least one of the second reflector structures is not in the presence of the third fluid.

In accordance with yet another aspect of the invention, a method is provided for detecting the presence of one or more fluids in a rotating component of a gas turbine engine. Light is emitted from a light source. Light emitted from the light source is received by a first reflector structure that is coupled to the rotating component, the first reflector structure having a first face and a second face. At least a substantial portion of the received light is reflected by the first reflector structure if the first reflector structure second face is in the presence of a first fluid and is not reflected by the first reflector structure if the first reflector structure second face is in the presence of a second fluid, the second fluid having an index of refraction that is greater than an index of refraction of the first fluid. At least a portion of any light reflected by the first reflector structure is received. The first reflector structure second face is determined to be not in the presence of the second fluid if the received portion of light reflected by the first reflector structure is greater than or equal to a first predetermined amount.

Light emitted from the light source may be received by a second reflector structure that is coupled to the rotating component and spaced circumferentially from the first reflector structure. The second reflector structure has a first face and a second face. At least a substantial portion of the received light is reflected by the second reflector structure if the second reflector structure second face is in the presence of the first fluid or the second fluid and is not reflected by the second reflector structure if the second reflector structure second face is in the presence of a third fluid, the third fluid having an index of refraction that is greater than the index of refraction of the second fluid. At least a portion of any light reflected by the second reflector structure is received. The second reflector structure second face is determined to be not in the presence of the third fluid if the received portion of light reflected by the second reflector structure is greater than or equal to a second predetermined amount.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, a specific preferred embodiment in which the invention may be practiced. It is to be understood that other embodiments may be utilized and that changes may be made without departing from the spirit and scope of the present invention.

Figure 1:
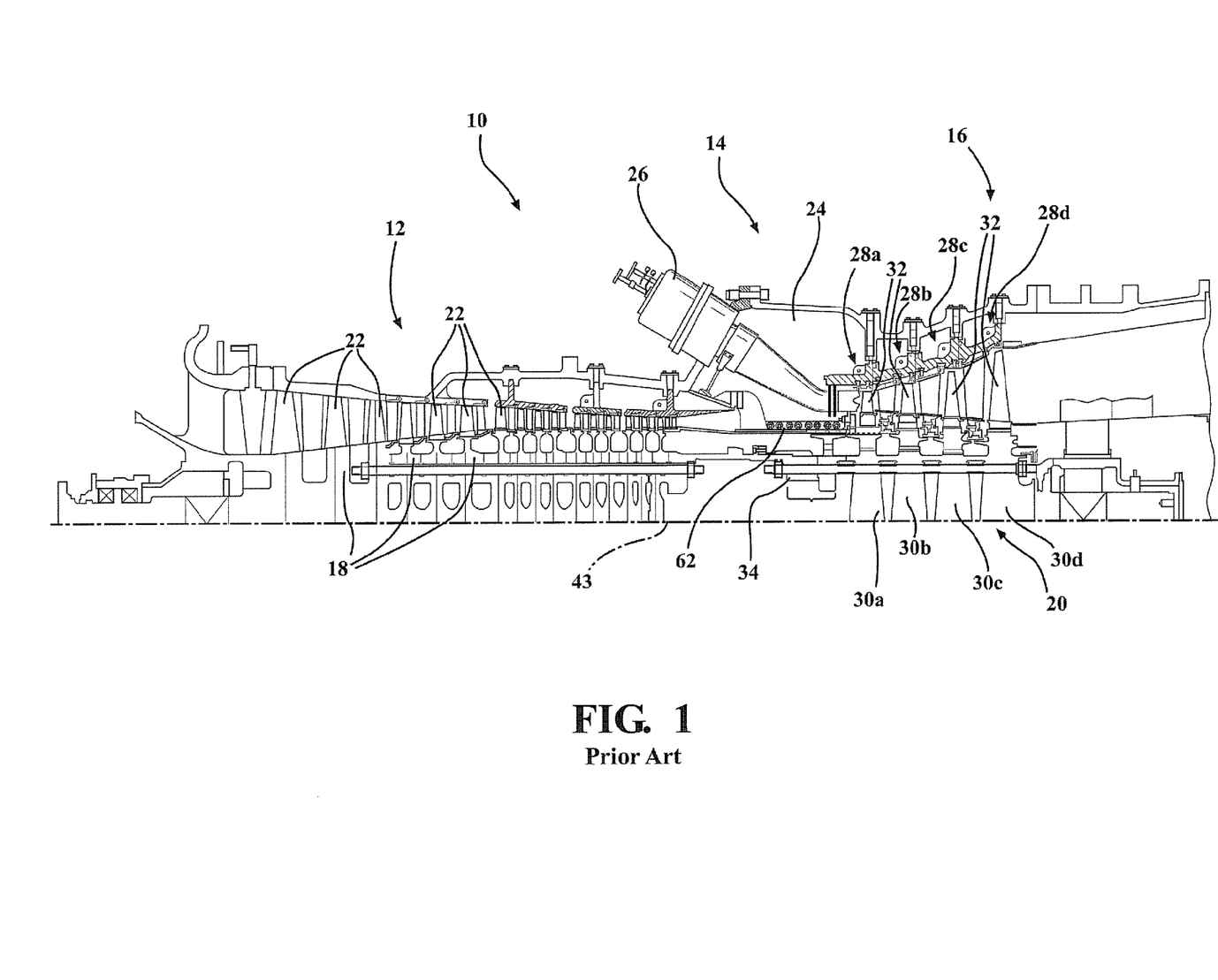
FIG. 1 is a cross-section view of a conventional gas turbine engine including a torque tube.

Referring to FIG. 1, a conventional gas turbine engine 10 is illustrated including a compressor section 12, a combustor section 14 and a turbine section 16. The compressor section 12 comprises a plurality of stages, each stage comprising a compressor disk 18 forming a portion of a rotor 20, and each compressor disk 18 supporting a row of compressor blades 22. Compressed exit air from the compressor section 12 is supplied to a combustor shell 24 of the combustor section 14 and is directed to one or more combustors 26 where the air is mixed with fuel and ignited to produce hot working gases for producing power in the turbine section 16.

The turbine section 16 includes a plurality of turbine stages, illustrated as first through fourth stages 28a, 28b, 28c, 28d. Each of the turbine stages 28a, 28b, 28c, 28d comprises a respective one of first through fourth turbine disks 30a, 30b, 30c, 30d that define a portion of the rotor 20, and each of the turbine disks 30a, 30b, 30c, 30d supports a plurality of blades 32 for converting the energy of the hot working gases into rotational movement of the rotor 20. The rotor 20 further comprises a torque tube 34 extending between the compressor section 12 and the turbine section 16 for transferring output power from the turbine section 16 to the compressor section 12, where a portion of the output power is used to drive the compressor disks 18 and blades 22, and the remaining portion of the output power is used to drive an output device, such as electrical generator (not shown) in a power generation plant.

Figure 2:
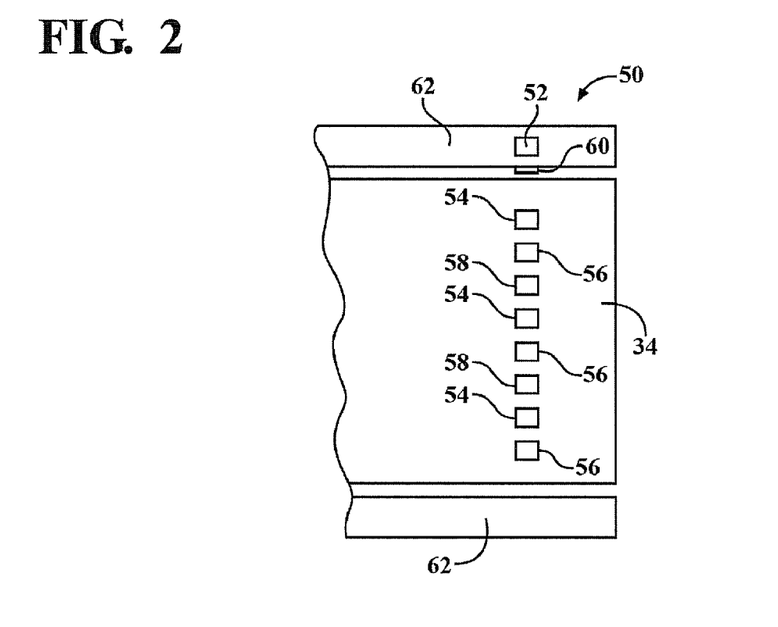
FIG. 2 is a schematic illustration of a fluid detection system associated with a torque tube of a gas turbine engine in accordance with an aspect of the present invention.

Referring to FIG. 2, a fluid detection system 50 is illustrated. The fluid detection system 50 is associated with a torque tube in the illustrated embodiment, such as the torque tube 34 illustrated in FIG. 1, for detecting one or more fluids in the torque tube 34. While the system 50 according to this aspect of the invention is associated with the torque tube 34, it is noted that the system 50 may be associated with other rotating components in the engine 10 for detecting one or more fluids therein or thereon, such as, for example by installing reflector structures, discussed below, in a machined cavity between rows of compressor or turbine blades or mounting the reflector structure to a blade to sense water/oil inside the rotating blade. The term "fluid" as used herein may refer to a liquid, a gas, or a combination of liquid and gas.

The system 50 comprises a light source 52 that emits light, a plurality of circumferentially spaced apart first reflector structures 54, a plurality of second reflector structures 56 circumferentially spaced apart from each other and from the first reflector structures 54, a plurality of third reflector structures 58 circumferentially spaced apart from each other and from the first and second reflector structures 54 and 56, and a reflection receiver structure 60, each of which will be described in detail herein.

The light source 52 and the reflection receiver structure 60 are coupled to non-rotating structure, such as a stationary shaft cover structure 62 disposed about the torque tube 34, and the first, second, and third reflector structures 54, 56, 58 are disposed in the torque tube 34 so as to rotate with the torque tube 34. As will be discussed herein, a direct line of sight is intermittently provided between the light source 52 and the first, second, and third reflector structures 54, 56, 58 for each revolution of the torque tube 34 and the first, second, and third reflector structures 54, 56, 58. A direct line of sight is also intermittently provided between the first, second, and third reflector structures 54, 56, 58 and the reflection receiver structure 60 for each revolution of the first, second, and third reflector structures 54, 56, 58. It is noted that the light source 52 and the reflection receiver structure 60 could be coupled to other non-rotating structure in the engine 10, so long as a direct line of sight (which line of sight may be intermittent) is provided between the light source 52 and the first, second, and third reflector structures 54, 56, 58 and between the reflection receiver structure 60 and the first, second, and third reflector structures 54, 56, 58.

Figure 3:
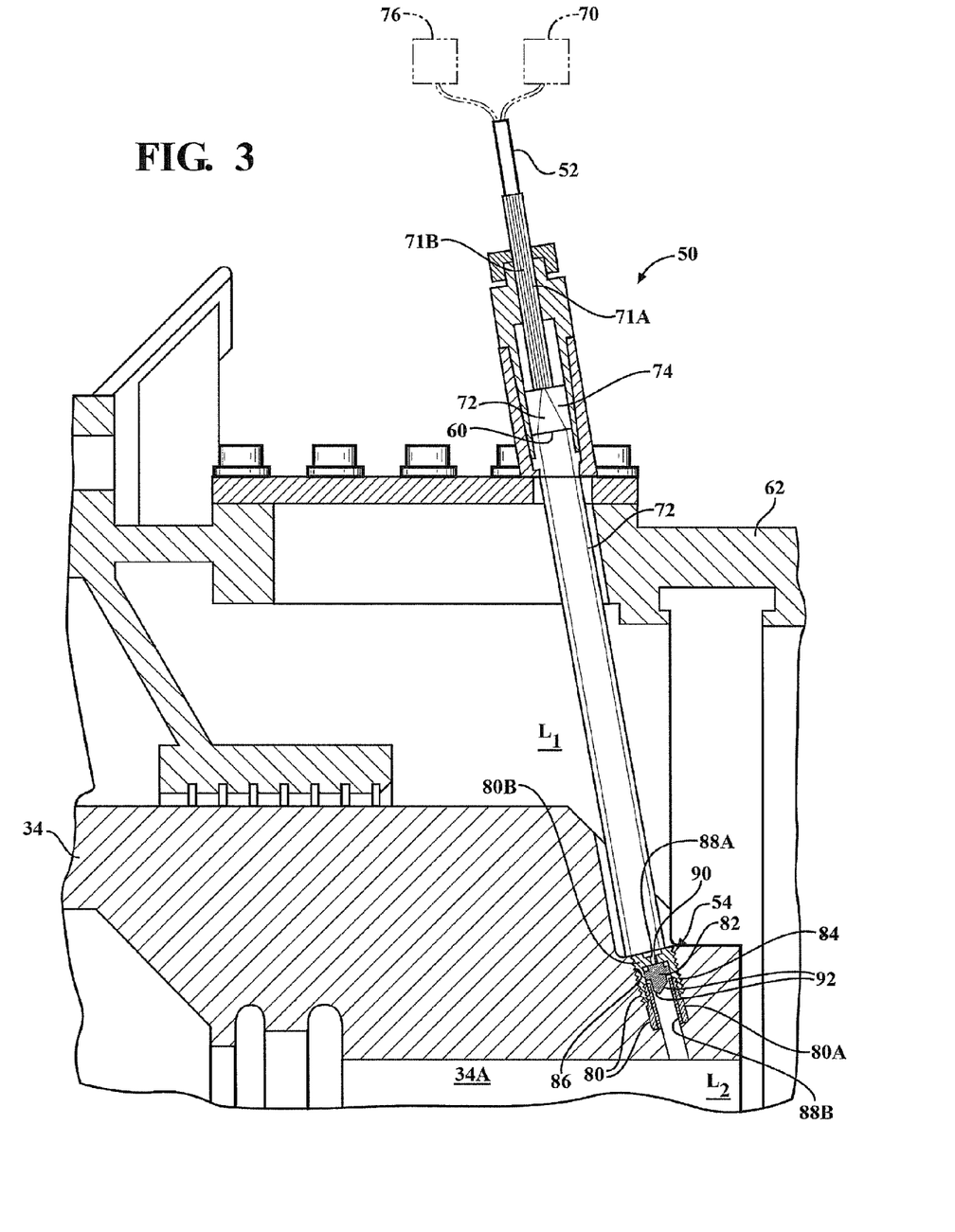
FIG. 3 is an enlarged cross sectional view of a portion of the torque tube and a reflector structure and a light source of the fluid detection system of FIG. 2.

Referring to FIG. 3, the light source 52 according to this embodiment comprises a laser source 70 that emits a laser beam 72 and one or more fibers 71A that carry the laser beam 72, although other suitable light sources may be used. The fibers 71A direct the laser beam 72 toward a lens 74, which lens 74 is coupled to the shaft cover structure 62 and receives the laser beam 72 from the fibers 71A. The lens 74 collimates the laser beam 72 and directs the collimated laser beam 72 to a predefined location for sequential exposure to the rotating first, second, and third reflector structures 54, 56, 58 (only a first reflector structure 54 is illustrated in FIG. 3), which reflector structures 54, 56, 58 are disposed in and rotate with the torque tube 34 as noted above.

The reflection receiver structure 60 according to one aspect of the invention comprises the lens 74, one or more fibers 71B, which may be bundled with the fibers 71A, and a data analysis device 76. As will be described in detail herein, the lens 74 receives reflected light and directs the received light to one or more of the fibers 71B, which fibers 71B carry the received light to the data analysis device 76. It is noted that the reflection receiver structure 60 may include a separate lens (not shown) for receiving the reflected light, rather than using the lens 74. It is noted that the lens 74 preferably provides multiple functions, i.e., collimates the laser beam 74 and receives the reflected light.

One of the first reflector structures 54 of the fluid detection system 50 will now be described, it being understood that the remaining first reflector structures 54 of the system 50 may be substantially identical to the first reflector structure 54 described herein. As shown in FIG. 3, the first reflector structure 54 comprises a housing 80 and a first corner cube prism 82, also known as a retroreflector, supported in the housing 80. The first corner cube prism 82 will hereinafter be referred to as the "first prism 82".

The housing 80 may comprise inner and outer pieces 80A and 80B that are coupled together, such as by a threaded fastening. The first prism 82 may be disposed between the inner and outer pieces 80A and 80B and then the inner and outer pieces 80A and 80B may be coupled together to secure the first prism 82 in the housing 80. The housing 80 in the embodiment shown comprises a threaded outer surface 84 that is received in a threaded opening 86 formed in the torque tube 34 to secure the first reflector structure 54 in the torque tube 34.

As shown in FIG. 3, the first prism 82 is exposed through openings 88A and 88B in the housing 80. Hence, a first face 90 (see also FIG. 4) of the first prism 82 is exposed to and is thus visible from a first location $L_1$ radially outwardly from the first reflector structure 54, and a second face 92 (see also FIG. 4) of the first prism 82 is exposed to and is thus visible from a second location $L_2$ radially inwardly from the first reflector structure 54. Preferably, the first face 90 is generally planar and positioned such that the incident laser beam 72 is substantially perpendicular when it strikes the first face 90, although it is noted that the laser beam 72 need not strike the first face 90 perpendicularly. The second face 92 comprises three mutually perpendicular, intersecting flat surfaces 92A-92C, see FIG. 4A. It is noted that the opening 86 formed in the torque tube preferably extends all the way to a hollow interior portion 34A of the torque tube 34, as shown in FIG. 3.

Figure 4:
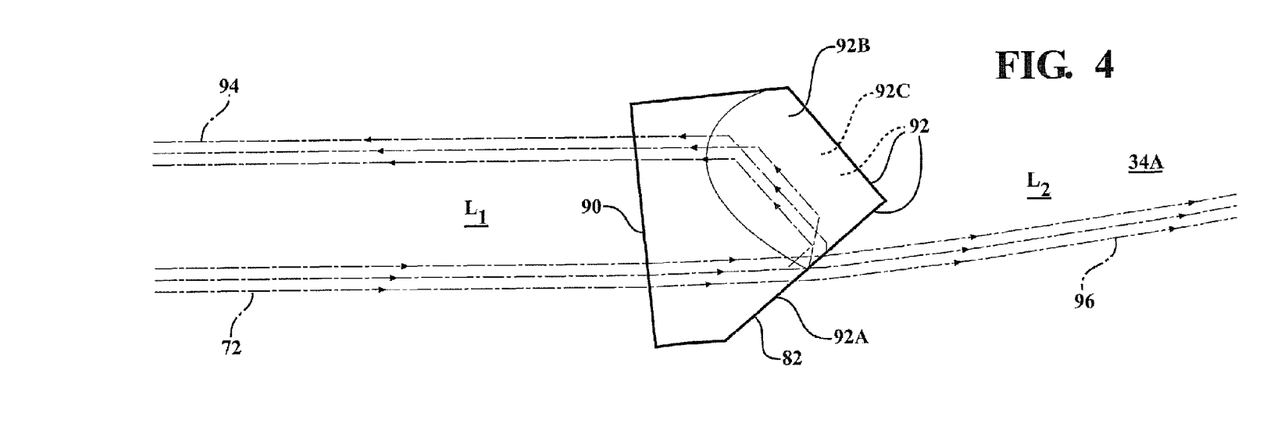
FIG. 4 illustrates a first type of reflector structure of the fluid detection system of FIG. 2.
Figure 4A:
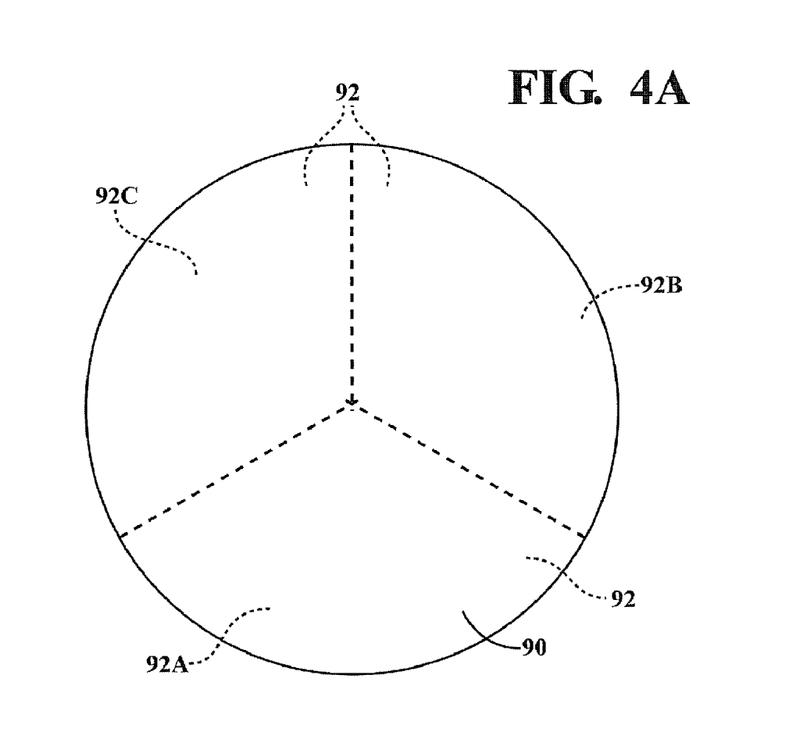
FIG. 4A is an end view of the reflector structure illustrated in FIG. 4.

Referring to FIG. 4, the first prism 82 of the first reflector structure 54 is formed from a material having a first index of refraction. It is noted that the housing 80 and the torque tube 34 have been removed in FIG. 4 to clearly illustrate the first prism 82. The first index of refraction is greater than an index of refraction of a first fluid to be sensed within the hollow interior portion 34A of the torque tube 34. In a preferred embodiment, the first index of refraction is greater than the index of refraction of the first fluid by at least a predetermined amount to facilitate a sufficient amount of reflected light, as will be discussed herein.

The predetermined amount may be at least about 1.23 times the index of refraction of the first fluid to be sensed. In one embodiment, the first fluid may comprise, for example, air, which has an index of refraction of about 1.0. Hence, the index of refraction of the material forming the first prism 82 may be about 1.23 or higher, i.e., 1.0×1.23=1.23. It is noted that the first fluid need not be air and could be any fluid. However, if a second fluid is to be sensed within the hollow interior portion 34A of the torque tube 34, the first fluid preferably has an index of refraction that is less that an index of refraction of the second fluid. The second fluid will be discussed below.

Assuming in this example that the first fluid is air, the material forming the first prism 82 may be, for example, fused silica, which has an index of refraction of about 1.459, which is greater than the index of refraction of air (about 1.0) by at least the predetermined amount (1.23). Since the index of refraction of the material forming the first prism 82 (fused silica in this example) is greater than the index of refraction of the first fluid (air in this example) by at least the predetermined amount, if the second face 92 of the first prism 82 is in the presence of the first fluid (air), at least a substantial portion of incident light 72 received by the first face 90 of the first prism 82 is reflected by the second face 92 of the first prism 82, as identified by reference number 94 in FIG. 4. This results based on the principal of total internal reflection, which is an optical phenomenon that occurs when a ray of light strikes a medium boundary at an angle larger than a particular critical angle with respect to a normal to the boundary surface, which boundary surface is defined by one of the first, second, and third surfaces 92A-92C (hereinafter referred to as the "one surface 92A-92C") of the second face 92 of the first prism 82.

The light reflected by the one surface 92A-92C of the first prism 82 is reflected by another one of the first, second, and third surfaces 92A-92C of the second face 92 of the first prism 82 to the remaining one of the first, second, and third surfaces 92A-92C, and then back toward the first face 90 of the first prism 82. The first prism 82 functions as a retroreflector and reflects the light 94 in a direction opposite to and substantially parallel to the incident light 72, see FIG. 4, i.e., the first reflector structure 54 reflects at least a substantial portion of the received light from the light source 52 if the second face 92 of the first prism 82 is in the presence of the first fluid.

The light 94 reflected by the first reflector structure 54 is directed at and is received by the lens 74 of the reflection receiver structure 60. The lens 74 directs the received, reflected light to the fibers 71B, which fibers 71B carry the light to the data analysis device 76, which monitors and analyzes the amount of the received, reflected light.

Alternatively, if the second face 92 of the first prism 82 is in the presence of a second or third fluid, e.g., water or oil, and the first index of refraction of the first prism 82 is not greater than or equal to the index of refraction of the second/third fluid by at least the predetermined amount, e.g., the index of refraction of water is about 1.33 and the index of refraction of one select type of oil is about 1.46, at least a substantial portion of incident light 72 received by the first face 90 of the first prism 82 is not internally reflected by the second face 92 of the first prism 82. Rather, the light passes through the one surface 92A-92C and is refracted, as identified by reference number 96 in FIG. 4. The refracted light 96 is therefore not reflected by the first prism 82 toward the lens 74 and is not received by the data analysis device 76.

Hence, the first reflector structure 54 can be used to determine if the second face 92 of the first prism 82 is in the presence of the second/third fluid (water or oil in the above-described embodiment). That is, if the reflection receiver structure 60 receives a first predetermined amount of light 94 reflected by the first reflector structure 54, it can be determined that the second face 92 of the first prism 82 is in the presence of air and is not in the presence of the second or the third fluid (water or oil). If the reflection receiver structure 60 does not receive the first predetermined amount of light reflected by the first reflector structure 54, it can be determined that the second face 92 of the first prism 82 is not in the presence of air and presumed to be in the presence of the second/third fluid, e.g., water, oil, or a combination thereof.

During operation of the engine 10, the rotation of the torque tube 34 causes the second/third fluid, if present in the hollow interior portion 34A of the torque tube 34, to move radially outwardly due to centrifugal force so as to come into contact with the second face 92 of the first prism 82. If it is determined that the second face 92 of the first prism 82 is in the presence of the second/third fluid (water or oil) as discussed above, it can be determined that the hollow interior portion 34A of the torque tube 34 contains the second/third fluid (water or oil).

Figure 5:
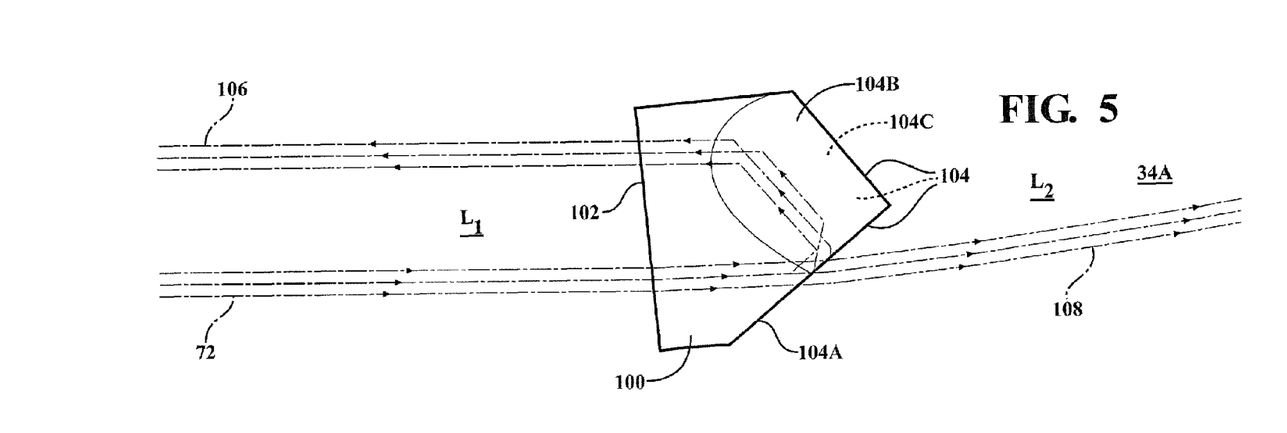
FIG. 5 illustrates a second type of reflector structure of the fluid detection system of FIG. 2.

Referring to FIG. 5, a second corner cube prism 100, also known as a retroreflector, of one of the second reflector structures 56 will now be described, it being understood that the remaining second reflector structures 56 may be substantially identical to the second reflector structure 56 described herein. The second corner cube prism 100 will hereinafter be referred to as the "second prism 100".

The second prism 100 is supported in a housing (not shown) that is received in an opening (not shown) in the torque tube 34 as discussed above with respect to the first prism 82. Similar to the first prism 82, a first face 102 of the second prism 100 is exposed to and is thus visible from the first location $L_1$, and a second face 104 of the second prism 100 is exposed to and is thus visible from the second location $L_2$. The first face 102 of the second prism 100 is preferably generally planar and positioned such that the incident laser beam 72 is substantially perpendicular when it strikes the first face 102, although the laser beam 72 need not strike the first face 102 perpendicularly. Similar to the first prism 82, the second face 104 comprises three mutually perpendicular, intersecting flat surfaces 104A-104C.

The second prism 100 of the second reflector structure 56 is formed from a material having a second index of refraction that is greater than the first index of refraction. The second index of refraction is also greater than an index of refraction of the second fluid to be sensed within the hollow interior portion 34A of the torque tube 34. In a preferred embodiment, the second index of refraction is greater than the index of refraction of the second fluid by at least a predetermined amount to facilitate a sufficient amount of reflected light, as will be discussed herein.

The predetermined amount may be at least about 1.23 times the index of refraction of the second fluid to be sensed. In one embodiment, the second fluid may comprise, for example, water, which has an index of refraction of about 1.33. Hence, the index of refraction of the material forming the second prism 100 may be about 1.635 or higher, i.e., 1.33×1.23=1.635. It is noted that the second fluid need not be water and could be any fluid having a greater index of refraction than the first fluid. However, if a third fluid is to be sensed within the hollow interior portion 34A of the torque tube 34, the second fluid preferably has an index of refraction that is less that an index of refraction of the third fluid. The third fluid will be discussed below.

Assuming that the second fluid is water, the material forming the second prism 100 may be, for example, S-LAL58 glass, which has an index of refraction of about 1.693, which is greater than the index of refraction of the first prism 82 and is also greater than the index of refraction of both air (1.0) and water (about 1.33) by at least the predetermined amount (1.23). Since the index of refraction of the material forming the second prism 100 (S-LAL58 glass in this example) is greater than the index of refraction of both the first fluid (air in this example) and the second fluid (water in this example) by at least the predetermined amount, if the second face 104 of the second prism 100 is in the presence of the first fluid (air) or the second fluid (water), at least a substantial portion of incident light 72 received by the first face 102 of the second prism 100 is reflected by the second face 104 of the second prism 100, as identified by reference number 106 in FIG. 5. This results based on the principal of total internal reflection, as discussed above. The boundary surface corresponding to the second prism 100 is defined by one of the first, second, and third surfaces (hereinafter referred to as the "one surface 104A-104C") of the second face 104 of the second prism 100.

The light reflected by the one surface 104A-104C of the second prism 100 is reflected by another one of the first, second, and third surfaces 104A-104C of the second face 104 of the second prism 100 to the remaining one of the first, second, and third surfaces 104A-104C, and then back toward the first face 102 of the second prism 100. The second prism 100 functions as a retroreflector and reflects the light 106 in a direction opposite to and substantially parallel to the incident light 72, see FIG. 5, i.e., the second reflector structure 56 reflects at least a substantial portion of the received light from the light source 52 if the second face 104 of the second prism 100 is in the presence of the first fluid (air) or the second fluid (water).

The light 106 reflected by the second reflector structure 56 is directed at and is received by the lens 74 of the reflection receiver structure 60. The lens 74 directs the received, reflected light to the fibers 71B, which fibers 71B carry the light to the data analysis device 76, which monitors and analyzes the amount of the received, reflected light.

Alternatively, if the second face 104 of the second prism 100 is in the presence of a third fluid, e.g., oil, and the second index of refraction of the second prism 100 is not greater than or equal to the index of refraction of the third fluid by at least the predetermined amount, e.g., the index of refraction of one select type of oil is about 1.46, at least a substantial portion of incident light 72 received by the first face 102 of the second prism 100 is not internally reflected by the second face 104 of the second prism 100. Rather, the light passes through the one surface 104A-104C and is refracted, as identified by reference number 108 in FIG. 5. The refracted light 105 is therefore not reflected by the second prism 100 toward the lens 74 and is not received by the data analysis device 76.

Hence, the second reflector structure 56 can be used to determine if the second face 104 of the second prism 100 is in the presence of the third fluid (oil in the above-described example). That is, if the reflection receiver structure 60 receives a second predetermined amount of light 106 reflected by the second reflector structure 56, it can be determined that the second face 104 of the second prism 100 is not in the presence of the third fluid (oil). If the reflection receiver structure 60 does not receive the second predetermined amount of light reflected by the second reflector structure 56, it can be determined that the second face 104 of the second prism 100 is in the presence of the third fluid, e.g., oil.

During operation of the engine 10, the rotation of the torque tube 34 causes the third fluid, if present in the hollow interior portion 34A of the torque tube 34, to move radially outwardly so as to come into contact with the second face 104 of the second prism 100. If it is determined that the second face 104 of the second prism 100 is in the presence of the third fluid (oil) as discussed above, it can be determined that the hollow interior portion 34A of the torque tube 34 contains the third fluid (oil).

Further, the first and second reflector structures 54 and 56 can collectively be used to determine which of the second and third fluids is in the torque tube 34, if it is determined that one of the second and third fluids is in the hollow interior portion 34A of the torque tube 34, i.e., with the use of the first reflector structure 54. For example, assume the reflection receiver structure 60 does not receive the first predetermined amount of reflected light 94 from at least one of the first reflector structures 54 to indicate that the second or the third fluid (water or oil) is present in the hollow interior portion 34A of the torque tube 34. The second reflector structure(s) 56 can then be used to determine whether the third fluid (oil) is in the torque tube 34, i.e., if the second predetermined amount of reflected light 106 is not received by the reflection receiver structure 60 from at least one of the second reflector structures 56, it can be determined that the third fluid (oil) is in the torque tube 34. If the second predetermined amount of reflected light is received by the reflection receiver structure 60 from at least one of the second reflector structures 56, it can be determined that the second fluid (water) is in the torque tube 34, i.e., since the first reflector structure(s) 54 determined that water or oil is in the torque tube 34, and the second reflector structure(s) 56 determined that oil is not in the torque tube 34, i.e., air or water is in the torque tube 34. It is noted that using multiple reflector structures 54, 56 of the same type yields the possibility of having one or more of the reflector structures 54, 56 of the same type reflecting light and one or more others of that same type not reflecting light. This could indicate that the detected fluid, i.e., the first, second, or third fluid, is not evenly distributed inside the torque tube 34, or that one or more of the reflector structures 54, 56 is not operating correctly.

Figure 6:
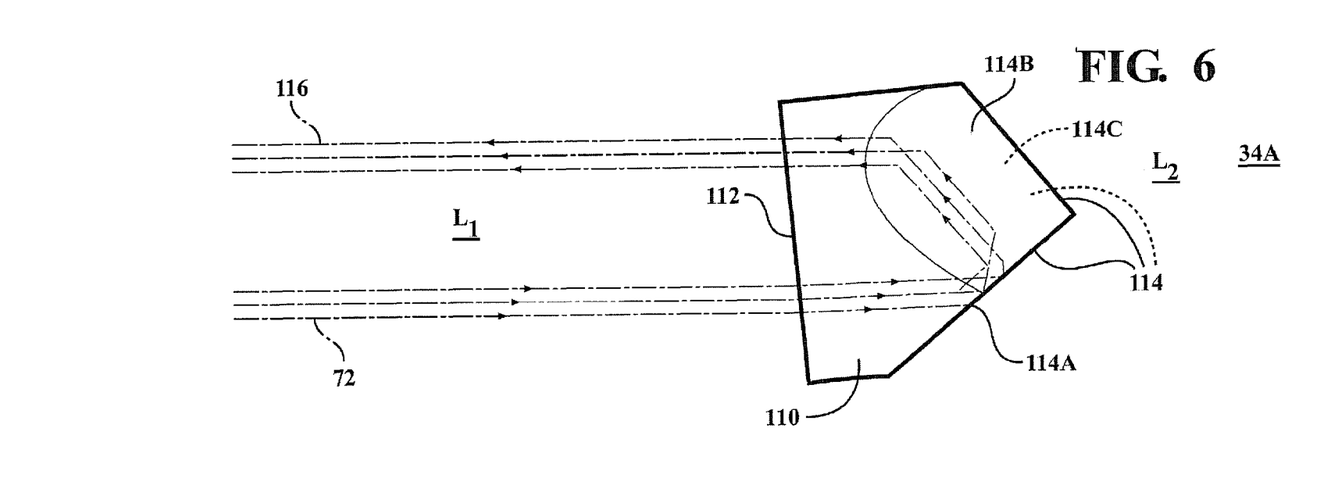
FIG. 6 illustrates a third type of reflector structure of the fluid detection system of FIG. 2.

Referring to FIG. 6, a third corner cube prism 110, also known as a retroreflector, of one of the third reflector structures 58 will now be described, it being understood that the remaining third reflector structures 58 may be substantially identical to the third reflector structure 58 described herein. The third corner cube prism 110 will hereinafter be referred to as the "third prism 110".

The third prism 110 is supported in a housing (not shown) that is received in an opening (not shown) in the torque tube 34 as discussed above with respect to the first prism 82. Similar to the first prism 82, a first face 112 of the third prism 110 is exposed to and is thus visible from the first location $L_1$, and a second face 114 of the third prism 110 is exposed to and is thus visible from the second location $L_2$. The first face 112 of the third prism 110 is preferably generally planar and positioned such that the incident laser beam 72 is substantially perpendicular when it strikes the first face 112, although the laser beam 72 need not strike the first face 112 perpendicularly. Similar to the first prism 82, the second face 114 comprises three mutually perpendicular, intersecting flat surfaces 114A-114C.

The third prism 110 of the third reflector structure 58 is formed from a material having a third index of refraction that is greater than the second index of refraction. The third index of refraction is also greater than an index of refraction of the third fluid to be sensed within the hollow interior portion 34A of the torque tube 34. In a preferred embodiment, the third index of refraction is greater than the index of refraction of the third fluid by at least a predetermined amount to facilitate a sufficient amount of reflected light, as will be discussed herein.

The predetermined amount may be at least about 1.23 times the index of refraction of the third fluid to be sensed, as will be discussed below. In one embodiment, the third fluid may comprise, for example, one select type of oil, which has an index of refraction of about 1.46. Hence, the index of refraction of the material forming the third prism 110 may be about 1.796 or higher, i.e., 1.46×1.23=1.796. It is noted that the third fluid need not be oil and could be any fluid having a greater index of refraction than the second fluid.

Assuming that the third fluid is oil having an index of refraction of about 1.46, the material forming the third prism 110 may be, for example, S-LAH79 glass, which has an index of refraction of about 2.003, which is greater than the index of refraction of the first and second prisms 82 and 100 and is also greater than the index of refraction of each of air (1.0), water (about 1.33), and the select oil (about 1.46) by at least the predetermined amount (1.23). Since the index of refraction of the material forming the third prism 110 (S-LAH79 glass in this example) is greater than the index of refraction of each of the first fluid (air in the example), the second fluid (water in this example), and the third fluid (oil having an index of refraction of 1.46 in this example) by at least the predetermined amount, if the second face 114 of the third prism 110 is in the presence of the first fluid (air), the second fluid (water), or the third fluid (oil), at least a substantial portion of any light received by the first face 112 of the third prism 110 is reflected by the second face 114 of the third prism 110, as identified by reference number 116 in FIG. 6. This results based on the principal of total internal reflection, as discussed above. The boundary surface corresponding to the third prism 110 is defined by one of the first, second, and third surfaces (hereinafter referred to as the "one surface 114A-114C") of the second face 114 of the third prism 110.

The light reflected by the one surface 114A-114C of the third prism 110 is reflected by another one of the first, second, and third surfaces 114A-114C of the second face 114 of the third prism 110 to the remaining one of the first, second, and third surfaces 114A-114C, and then back toward the first face 112 of the third prism 110. The third prism 110 functions as a retroreflector and reflects the light 116 in a direction opposite to and substantially parallel to the incident light 72, see FIG. 6, i.e., the third reflector structure 58 reflects at least a substantial portion of the received light from the light source 52 if the second face 114 of the third prism 110 is in the presence of the first fluid (air), the second fluid (water), or the third fluid (oil).

The light 116 reflected by the third reflector structure 58 is directed at and is received by the lens 74 of the reflection receiver structure 60. The lens 74 directs the received, reflected light to the fibers 71B, which fibers 71B carry the light to the data analysis device 76, which monitors and analyzes the amount of the received, reflected light.

Since the second face 114 of the third prism 110 will be in the presence of one or more of these fluids, i.e., air, water, or oil, under substantially all operating conditions, the third reflector structures 58 can be used as a check to verify that the fluid detection system 50 is working properly. That is, if the reflection receiver structure 60 receives a third predetermined amount of light 116 reflected by the third reflector structure 58, it can be determined that the components of the fluid detection system 50 are working properly, i.e., the light source 52 is emitting light, the third reflector structures 58 are receiving and reflecting the light from the light source 52, and the reflection receiver structure 60 is receiving light 116 reflected from the third reflector structure 58.

During operation of the engine 10, the rotor 20 (including the torque tube 34) rotates and causes corresponding rotation of the first, second, and third reflector structures 54, 56, and 58. The light source 52 emits light in the form of a laser beam 72 in this embodiment. The lens 74 collimates the laser beam 72 and directs the collimated laser beam 72 to the rotating reflector structures 54, 56, and 58. For each rotational pass of the reflector structures 54, 56, and 58, the first faces 90, 102, and 112 of the respective prisms 82, 100, and 110 receive light from the laser beam 72. The received light passes through the prisms 82, 100, and 110 and contacts the second faces 92, 104, and 114 of the respective prisms 82, 100, and 110.

Depending on the fluid that is present on the radially inner surfaces of the second faces 92, 104, and 114 of the respective prisms 82, 100, 110, i.e., the exposed radially inner sides thereof, the received light is either reflected or not reflected, i.e., refracted, by the second faces 92, 104, and 114 of the respective prisms 82, 100, and 110, as discussed in detail above.

At least a portion of any light reflected by the second faces 92, 104, and 114 of the respective prisms 82, 100, 110, is directed at and received by the reflection receiver structure 60. Depending on the amount of light received by the reflection receiver structure 60 from each of the reflector structures 54, 56, and 58, it can be determined whether the second faces 92, 104, and 114 of the respective prisms 82, 100, and 110 are in the presence of the first, second, or third fluids, as discussed above.

The fluid detection system 50 can be used to determine if undesirable fluids, such as water and/or oil, are present in the hollow interior portion 34A of the torque tube 34. The system 50 is operational without physical contact between the light source 52 and the reflector structures 54, 56, and 58, and also without physical contact between the reflector structures 54, 56, and 58 and the reflection receiver structure 60. Hence, rubbing contact between these components is avoided, which could otherwise lead to damage/destruction of the system 50. Further, since the system 50 uses light as the detection medium and not current or voltage, the system 50 is substantially insensitive to electromechanical interference, as may typically be generated by the engine 10.

Further, since the reflector structures 54, 56, and 58 reflect the light from the laser beam 72 in the opposite direction from which it is received, the lens 74 is able to function as both a light collimator and a reflected light receiver, as discussed above. Hence, the overall size of the system 50 is compact such that the system 50 is able to be employed in confined spaces. Moreover, the system 50 is generally not sensitive to misalignment, as the laser beam 72 from the laser source 70 is reflected by the reflector structures 54, 56, and 58 back toward the lens 74 regardless of the incidence angle.

Figure 7:
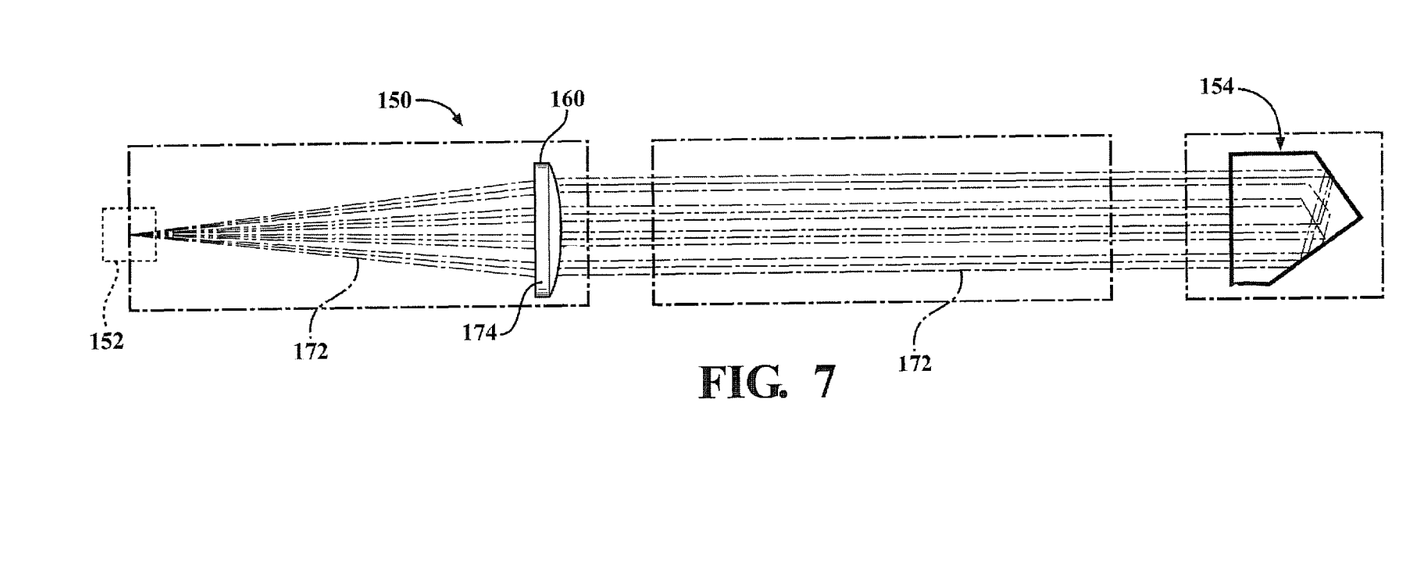
FIG. 7 illustrates a fluid detection system according to another embodiment of the invention.

Referring now to FIG. 7, a light source 152 for a fluid detection system 150 according to another embodiment of the invention is shown. In this embodiment, the light source 152 emits light 172 that is received and collimated by a lens 174. The lens 174 directs the collimated light 172 to reflector structures (only one reflector structure 154 is illustrated in FIG. 7), which reflector structures reflect or refract the light as discussed above with respect to FIGS. 4-6. The lens 174, also functioning as a component of a reflection receiver structure 160, receives light reflected by the reflector structures as discussed above. The light received by the reflection receiver structure 160 is then transmitted to a data analysis device (not shown), which tracks and analyses the data to determine what type of fluid is present in rotating structure (not shown in this embodiment), such as a torque tube, as discussed above.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system for detecting the presence of one or more fluids in a rotating component of a gas turbine engine, the system comprising:
   a light source that emits light;
   a first reflector structure coupled to the rotating component, said first reflector structure having a first face and a second face, said first face receiving light from said light source, wherein said first reflector structure:
   reflects at least a substantial portion of the received light from said light source if said second face is in the presence of a first fluid; and
   does not reflect a substantial portion of the received light from said light source if said second face is in the presence of a second fluid, the second fluid having an index of refraction that is greater than an index of refraction of the first fluid; and
   a reflection receiver structure that receives light reflected by said first reflector structure, wherein if said reflection receiver structure receives a first predetermined amount of light reflected by said first reflector structure it can be determined that said second face of said first reflector structure is not in the presence of the second fluid.

2. The system of claim 1, wherein said reflection receiver structure comprises a lens.

3. The system of claim 2, wherein said lens collimates the light from said light source and directs the collimated light toward said first reflector structure.

4. The system of claim 1, wherein said light source comprises a laser source that emits a laser beam.

5. The system of claim 1, wherein said first reflector structure functions as a retroreflector when said first reflector structure second face is in the presence of the first fluid.

6. The system of claim 5, wherein said reflector structure comprises a corner cube prism.

7. The system of claim 1, wherein said light source does not rotate with the rotating component and said first reflector structure.

8. The system of claim 1, wherein the first fluid is air and the second fluid is one of water and oil.

9. The system of claim 1, further comprising a second reflector structure coupled to the rotating component and spaced circumferentially from said first reflector structure, said second reflector structure having a first face and a second face, said first face receiving light from said light source, wherein said second reflector structure:
- reflects at least a substantial portion of the received light from said light source if said second face is in the presence of the first fluid;
- reflects at least a substantial portion of the received light from said light source if said second face is in the presence of the second fluid;
- does not reflect a substantial portion of the received light from said light source if said second face is in the presence of a third fluid, the third fluid having an index of refraction that is greater than the index of refraction of the second fluid; and
- wherein said reflection receiver structure receives light reflected by said second reflector structure, and wherein if said reflection receiver structure receives a second predetermined amount of light reflected by said second reflector structure it can be determined that said second face of said second reflector structure is not in the presence of the third fluid.

10. The system of claim 9, wherein the first fluid is air, the second fluid is water, and the third fluid is a type of oil.

11. The system of claim 9, further comprising a third reflector structure coupled to the rotating component and spaced circumferentially from said first and second reflector structures, said third reflector structure having a first face and a second face, said first face receiving light from said light source, wherein said third reflector structure:
- reflects at least a substantial portion of the received light from said light source if said second face is in the presence of the first fluid;
- reflects at least a substantial portion of the received light from said light source if said second face is in the presence of the second fluid;
- reflects at least a substantial portion of the received light from said light source if said second face is in the presence of the third fluid; and
- wherein said reflection receiver structure receives light reflected by said third reflector structure, and wherein if said reflection receiver structure receives a third predetermined amount of light reflected by said third reflector structure it can be determined that the system is functioning properly.

12. The system of claim 11, wherein:
- said first reflector structure comprises a corner cube prism formed from a first material having a first index of refraction;
- said second reflector structure comprises a corner cube prism formed from a second material having a second index of refraction greater than the first index of refraction; and
- said third reflector structure comprises a corner cube prism formed from a third material having a third index of refraction greater than the second index of refraction.

13. A system for detecting the presence of one or more fluids in a rotating component of a gas turbine engine, the system comprising:
- a light source that emits light;
- at least one first reflector structure coupled to the rotating component, each said first reflector structure having a first face and a second face, said first face receiving light from said light source, wherein each said first reflector structure:
  - reflects at least a substantial portion of the received light from said light source if said second face is in the presence of a first fluid; and
  - does not reflect a substantial portion of the received light from said light source if said second face is in the presence of a second fluid;
- at least one second reflector structure coupled to the rotating component and spaced circumferentially from each said first reflector structure, each said second reflector structure having a first face and a second face, said first face receiving light from said light source, wherein each said second reflector structure:
  - reflects at least a substantial portion of the received light from said light source if said second face is in the presence of the first fluid;
  - reflects at least a substantial portion of the received light from said light source if said second face is in the presence of the second fluid, the second fluid having an index of refraction that is greater than an index of refraction of the first fluid; and
  - does not reflect a substantial portion of the received light from said light source if said second face is in the presence of a third fluid, the third fluid having an index of refraction that is greater than the index of refraction of the second fluid; and
- a reflection receiver structure that receives light reflected by each of said first and second reflector structures, wherein:
  - if said reflection receiver structure receives a first predetermined amount of light reflected by at least one of said first reflector structures it can be determined that said second face of said at least one of said first reflector structures is not in the presence of the second fluid; and
  - if said reflection receiver structure receives a second predetermined amount of light reflected by at least one of said second reflector structures it can be determined that said second face of said at least one of said second reflector structures is not in the presence of the third fluid.

14. The system of claim 13, wherein said reflection receiver structure comprises a lens, and wherein said lens collimates the light from said light source and directs the collimated light toward said first and second reflector structures.

15. The system of claim 14, wherein said light source comprises a laser source that emits a laser beam.

16. The system of claim 13, wherein:
- each said first reflector structure comprises a corner cube prism formed from a first material having a first index of refraction; and
- each said second reflector structure comprises a corner cube prism formed from a second material having a second index of refraction greater than the first index of refraction.

17. The system of claim 13, wherein the first fluid is air, the second fluid is water, and the third fluid is a type of oil.

18. The system of claim 13, further comprising at least one third reflector structure coupled to the rotating component and spaced circumferentially from each of said first and second reflector structures, each said third reflector structure having a first face and a second face, said first face receiving light from said light source, wherein each said third reflector structure:
- reflects at least a substantial portion of the received light from said light source if said second face is in the presence of the first fluid;
- reflects at least a substantial portion of the received light from said light source if said second face is in the presence of the second fluid; and
- reflects at least a substantial portion of the received light from said light source if said second face is in the presence of the third fluid; and
- wherein said reflection receiver structure receives light reflected by each said third reflector structure, and wherein if said reflection receiver structure receives a third predetermined amount of light reflected by at least one of said third reflector structures it can be determined that the system is functioning properly.

19. A method for detecting the presence of one or more fluids in a rotating component of a gas turbine engine, the method comprising:
- emitting light from a light source;
- receiving light emitted from the light source by a first reflector structure that is coupled to the rotating component, the first reflector structure having a first face and a second face, wherein at least a substantial portion of the received light is reflected by the first reflector structure if the first reflector structure second face is in the presence of a first fluid and is not reflected by the first reflector structure if the first reflector structure second face is in the presence of a second fluid, the second fluid having an index of refraction that is greater than an index of refraction of the first fluid;
- receiving at least a portion of any light reflected by the first reflector structure; and
- determining that the first reflector structure second face is not in the presence of the second fluid if the received portion of light reflected by the first reflector structure is greater than or equal to a first predetermined amount.

20. The method of claim 19, further comprising:
- receiving light emitted from the light source by a second reflector structure that is coupled to the rotating component and spaced circumferentially from the first reflector structure, the second reflector structure having a first face and a second face, wherein at least a substantial portion of the received light is reflected by the second reflector structure if the second reflector structure second face is in the presence of the first fluid or the second fluid and is not reflected by the second reflector structure if the second reflector structure second face is in the presence of a third fluid, the third fluid having an index of refraction that is greater than the index of refraction of the second fluid;
- receiving at least a portion of any light reflected by the second reflector structure; and
- determining that the second reflector structure second face is not in the presence of the third fluid if the received portion of light reflected by the second reflector structure is greater than or equal to a second predetermined amount.

* * * * *